United States Patent
Grüebler et al.

(10) Patent No.: US 12,396,885 B2
(45) Date of Patent: Aug. 26, 2025

(54) RETRACTABLE BACKFLUSH INSTRUMENT

(71) Applicant: Alcon Inc., Fribourg (CH)

(72) Inventors: Reto Grüebler, Greifensee (CH);
Simon Nicola Kunz, Zurich (CH);
Niccolo Maschio, Winterthur (CH);
Christoph Siegenthaler, Eschenz (CH)

(73) Assignee: Alcon Inc., Fribourg (CH)

( * ) Notice: Subject to any disclaimer, the term of this patent is extended or adjusted under 35 U.S.C. 154(b) by 932 days.

(21) Appl. No.: 17/457,990

(22) Filed: Dec. 7, 2021

(65) Prior Publication Data

US 2022/0192875 A1    Jun. 23, 2022

Related U.S. Application Data

(60) Provisional application No. 63/126,823, filed on Dec. 17, 2020.

(51) Int. Cl.
*A61F 9/007* (2006.01)
*A61M 1/00* (2006.01)

(52) U.S. Cl.
CPC ......... *A61F 9/00736* (2013.01); *A61M 1/743* (2021.05); *A61M 1/76* (2021.05); *A61B 2217/005* (2013.01)

(58) Field of Classification Search
CPC ...... A61F 9/00736; A61F 2009/00874; A61M 1/743; A61M 1/76; A61M 1/7411; A61M 1/774; A61M 1/87; A61M 2210/0612; A61B 2217/005
See application file for complete search history.

(56) References Cited

U.S. PATENT DOCUMENTS

| | | | |
|---|---|---|---|
| 9,192,515 | B2 | 11/2015 | Papac |
| 9,730,834 | B2 | 8/2017 | Charles |
| 9,731,065 | B2 | 8/2017 | Bourne |
| 9,750,637 | B2 | 9/2017 | Schaller |
| 9,757,536 | B2 | 9/2017 | Abt |
| 9,878,075 | B2 | 1/2018 | Sussman |
| 2007/0260173 | A1 | 11/2007 | Boukhny |
| 2008/0167604 | A1 | 7/2008 | Hong |

(Continued)

FOREIGN PATENT DOCUMENTS

CN         202426711 U         9/2012

OTHER PUBLICATIONS

Alcon Global Vitreoretinal Product Catalog, 2014 (pp. 41-48).
(Continued)

*Primary Examiner* — Theodore J Stigell

(57) ABSTRACT

Certain embodiments provide an apparatus comprising a hand-piece, an outer tube coupled to the hand-piece, an inner tube housed within the outer tube and having a distal end coupled to a soft tip and a proximal end coupled to an adapter, a proximal end of the adapter coupled to a distal end of a valve, the valve slidably coupled to the hand-piece, and a core slidably coupled to the hand-piece and having a distal end coupled to a proximal end of the valve. To retract the soft tip, the valve is retracted, causing the adapter, the valve, and the core to slidably retract in a proximal direction in relation to the hand-piece, and to extend the soft tip, the valve is protracted, causing the adapter, the valve, and the core to slidably protract in a distal direction in relation to the hand-piece.

13 Claims, 4 Drawing Sheets

(56) References Cited

U.S. PATENT DOCUMENTS

| | | |
|---|---|---|
| 2016/0067091 A1 | 3/2016 | Wells |
| 2018/0296391 A1 | 10/2018 | Charles |
| 2019/0374248 A1 | 12/2019 | Grueebler |
| 2020/0188561 A1* | 6/2020 | Grueebler ............... A61M 1/85 |
| 2020/0397476 A1 | 12/2020 | Schaller |
| 2020/0397477 A1 | 12/2020 | Schaller |

OTHER PUBLICATIONS

DORC: Focus on Highlights catalog, 2012, pp. 9-11, 20, 34, 35.
https://www.vitreq.com/uploads/brochures/Vitreq_BVI_Brochure_Backflush_2018.pdf (accessed May 29, 2020, appears to be dated Jun. 2018 (8 pages).
MedOne Backflush Cannulas brochure, dated 2018 (1 page).
MedOne Brochure, "Exactly What Your Looking For—High Quality Instruments for Vitreoretinal Surgery," 2012, 12pages.

* cited by examiner

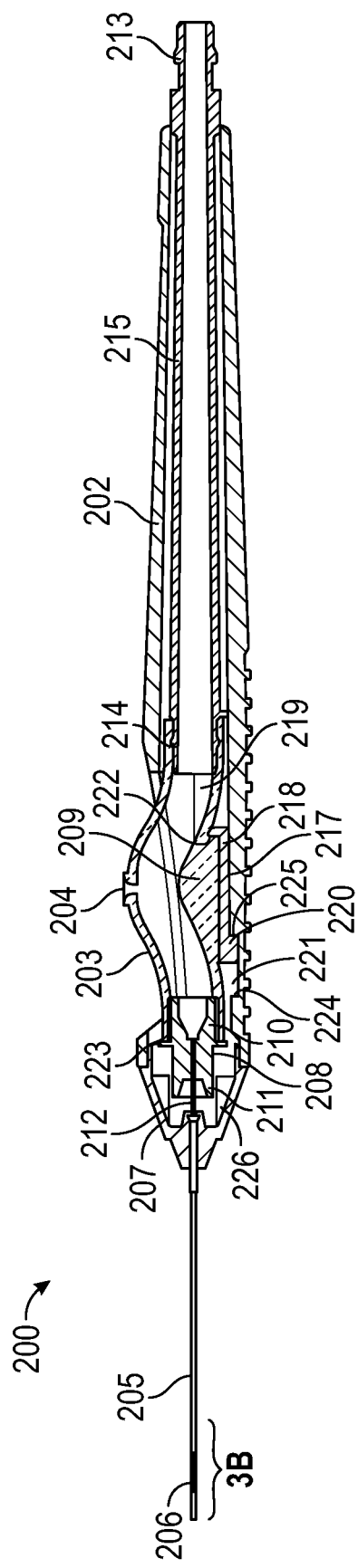
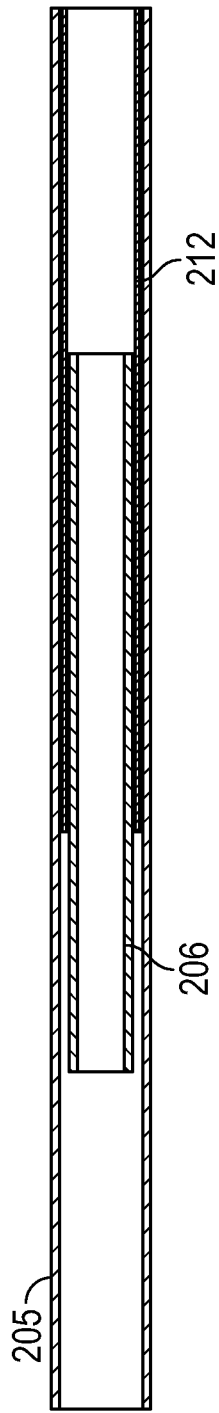
FIG. 3A
FIG. 3B

RETRACTABLE BACKFLUSH INSTRUMENT

PRIORITY CLAIM

This application claims the benefit of priority of U.S. Provisional Patent Application Ser. No. 63/126,823 titled "A RETRACTABLE BACKFLUSH INSTRUMENT," filed on Dec. 17, 2021, whose inventors are Reto Grüebler, Simon Nicola Kunz, Niccolo Maschio and Christoph Siegenthaler, which is hereby incorporated by reference in its entirety as though fully and completely set forth herein.

TECHNICAL FIELD

The present disclosure relates generally to a retractable backflush instrument.

BACKGROUND

A backflush instrument is generally used during surgery (e.g., ophthalmic surgery) for vacuuming or aspirating fluids (e.g., balanced salt solution (BSS), silicone oil, perfluorocarbon (PFC)) out of a body part (e.g., a patient's eye). For example, during certain ophthalmic surgeries, a backflush instrument may be used for extracting fluids, internal drainage of subretinal fluid, retinal fold manipulation, simultaneous or sequential exchanges (e.g., fluid-air, air-gas, fluid-gas, fluid-PFC, PFC-gas, etc.). Certain backflush instruments comprise a soft, distal tip to ensure that the body part, or any tissue thereof, is not damaged when the backflush instrument makes contact with the body part or the tissue. In one example, as part of a surgery, the backflush instrument is inserted into a cannula, such as a valved cannula, in order to introduce the backflush instrument into the body part. Inserting a backflush instrument with a soft tip into a cannula, however, may be challenging and may cause damage to the backflush instrument. For example, when the backflush instrument is being inserted through the valve of a valved cannula, the soft tip may bend and get stuck in the trocar cannula. In certain cases, the soft tip may even shear off the backflush instrument if the soft tip bends excessively.

BRIEF SUMMARY

The present disclosure relates generally to a retractable backflush instrument.

Certain embodiments described herein provide an apparatus comprising a hand-piece, an outer tube having a proximal end coupled to a distal end of the hand-piece, an inner tube housed within the outer tube and having a distal end coupled to a soft tip and a proximal end coupled to an adapter, wherein in a fully extended state, the soft tip at least partially extends beyond a distal end of the outer tube, the adapter slidably coupled to the distal end of the hand-piece, the adapter having a proximal end coupled to a distal end of a valve and a distal end coupled to the proximal end of the inner tube, the valve housed inside the hand-piece and having a distal end coupled to a proximal end of the adapter, and a core housed by and slidably coupled to the hand-piece, the core having a distal end coupled to a proximal end of the valve. To retract the soft tip, the valve is retracted, causing the adapter, the valve, and the core to slidably retract in a proximal direction in relation to the hand-piece, and to extend the soft tip, the valve is protracted, causing the adapter, the valve, and the core to slidably protract in a distal direction in relation to the hand-piece.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 3A illustrates a cross-sectional view of the backflush instrument of FIG. 2A in a retracted state, according to some embodiments.

FIG. 3B is an enlarged cross-sectional view of a distal portion of FIG. 3A illustrating a retracted soft tip, according to some embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a retractable backflush instrument.

As described above, inserting a backflush instrument with a soft tip into a cannula, such as a valved cannula can be challenging and may cause damage to the soft tip of the backflush instrument. Particular embodiments described in the present disclosure attempt to overcome these deficiencies by providing a slidable valve for retracting the soft tip prior to the instrument's insertion into a valved cannula, thereby preventing the soft tip from bending or being damaged during the insertion.

Figure 1:
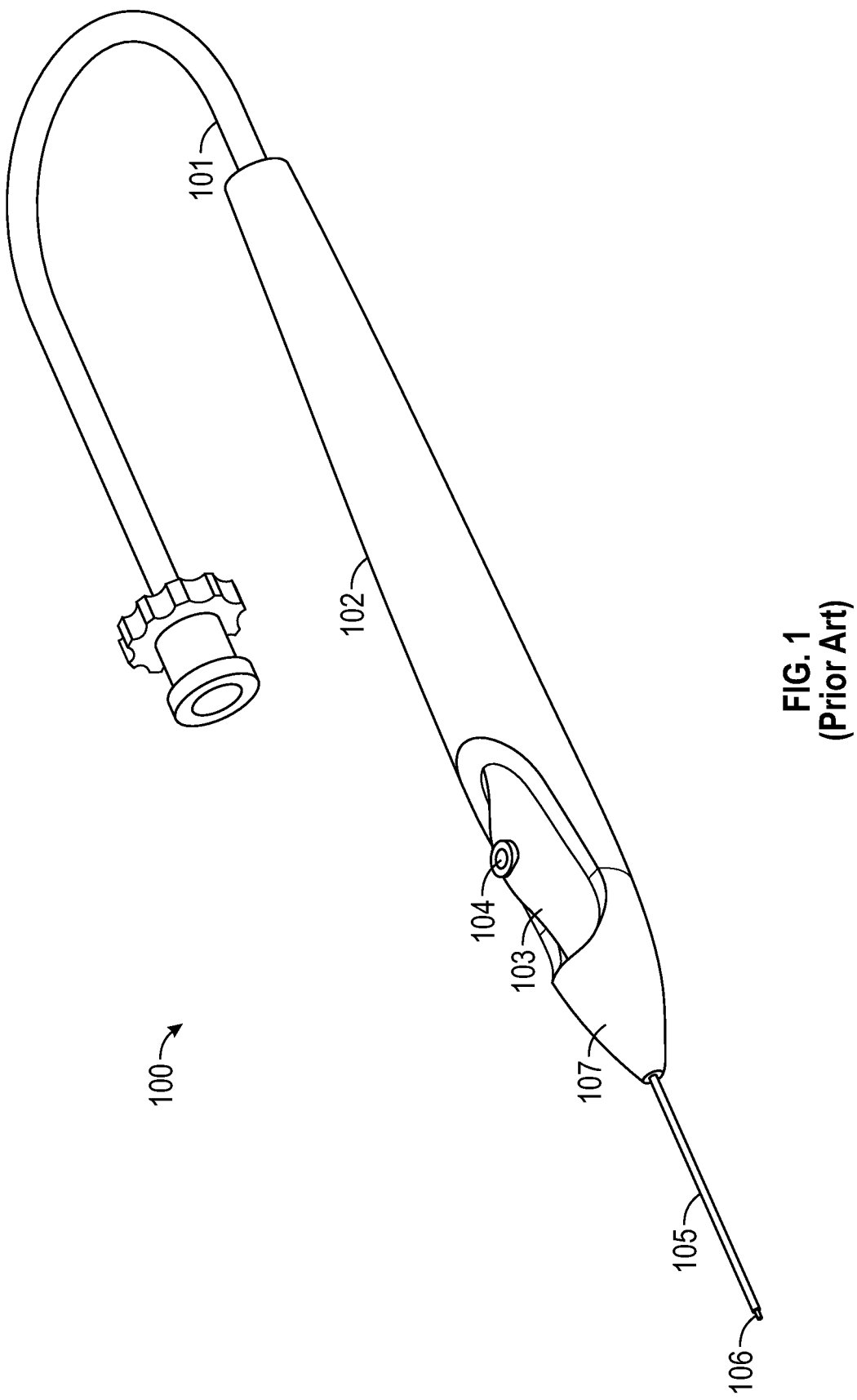
FIG. 1 illustrates a prior art example of a backflush instrument.

FIG. 1 illustrates a prior art example of a backflush instrument 100 comprising connector 101, hand-piece 102, outer tube 105, and a soft tip 106 that extends beyond the distal end of outer tube 105. The soft tip 106 of the backflush instrument 100 is not retractable. The proximal end of the outer tube 105 is coupled to a cap 107 located at a distal end of the hand-piece 102. Cap 107 is coupled to valve 103, which is hose-shaped and directly or indirectly (e.g., through some other elements within hand-piece 102) coupled to connector 101. As a result, valve 103 provides a fluidic connection between the outer tube 105 and connector 101. Valve 103 also comprises a hole 104, whose functionality varies depending on the mode in which backflush instrument 100 is operating. For example, backflush instrument 100 may be used in an active aspiration mode or a passive aspiration mode, as described below.

It should be noted that although various components are described herein with a certain shape (such as hose-shaped or cylindrical), the components may also take other similar, appropriate shapes as would be understood by one of ordinary skill in the art.

Connector 101 connects hand-piece 102 to a surgical console with an aspiration and/or irrigation mechanism. In one example, a user, such as a surgeon, uses hand-piece 102 to guide the tip of backflush instrument 100, including outer tube 105 and soft tip 106, at least partially through a cannula and into a body part. Once inside the body part, backflush instrument 100 engages in certain operations, such as vacuuming or aspirating material (e.g., BSS, oil, or other fluids, etc.) out of the body part. During such operations, fluid flows through connector 101, valve 103, and outer tube 105.

As described above, in particular embodiments, backflush instrument 100 may have two modes of operation: an active aspiration mode and a passive aspiration mode. In the active aspiration mode, backflush instrument 100 may be connected, through connector 101, to a surgical console that may actively aspirate fluids. In the active aspiration mode, the surgeon covers hole 104 (e.g., with a finger) to prevent air from being aspirated through hole 104.

In the passive aspiration mode, backflush instrument 100 is used without being connected to any surgical console through connector 101. In such an embodiment, because pressure within a body part (e.g., a patient's eye) is higher than the atmospheric pressure, when a surgeon inserts backflush instrument 100 into the body part, fluids may flow from the body part into backflush instrument 100 and exit through hole 104. In other words, in the passive aspiration mode, hole 104 may be used as a fluid outlet.

The outer tube 105 is typically made of rigid material, such as a metal (e.g., stainless steel). Soft tip 106 is typically made of soft and flexible material (e.g., silicone, rubber, polyurethane (PUR)) as to not damage the body part with which backflush instrument 100 comes in contact. However, it may be cumbersome or impossible for a surgeon to insert backflush instrument 100 with soft tip 106 through a valved cannula. This is because when the tip of backflush instrument 100 is being pushed through the valve of the valved cannula, enough opposite force may be applied by the valve to soft tip 106 so as to bend soft tip 106. In certain cases, if the surgeon forces the bent soft tip 106 through the cannula, soft tip 106 may even separate or shear off from the outer tube 105.

Figure 2A:
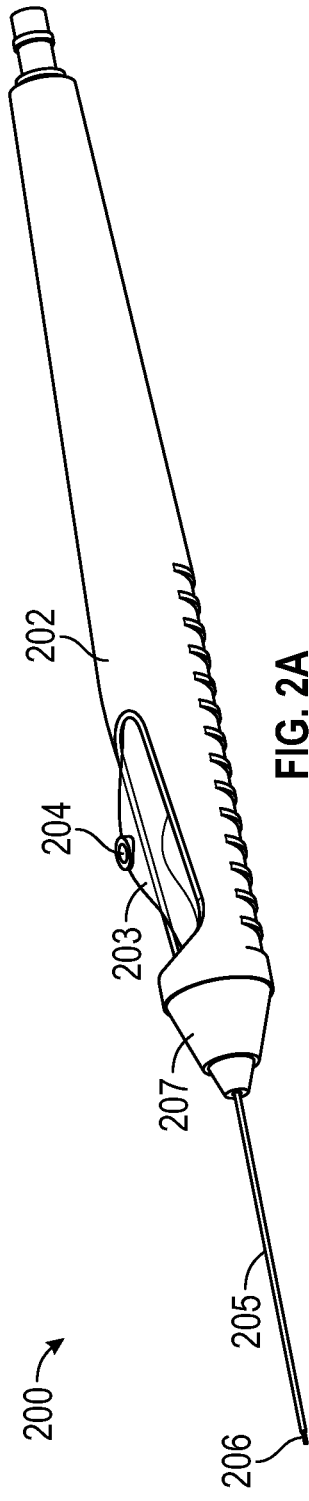
FIG. 2A illustrates an example retractable backflush instrument, according to some embodiments.
Figure 2B:
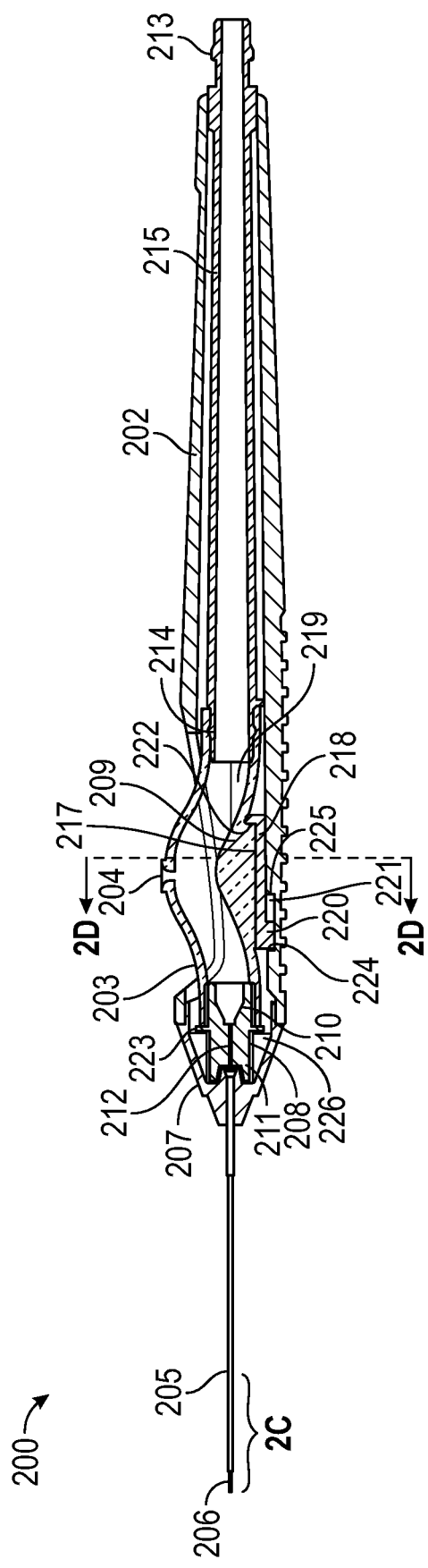
FIG. 2B illustrates a cross-sectional view of the backflush instrument of FIG. 2A in an extended state, according to some embodiments.

Accordingly, certain embodiments of the present disclosure provide a backflush instrument with a retractable soft tip attached to a cylindrical, hollow inner tube (e.g., inner tube 212 shown in FIG. 2B). Using such a backflush instrument, a surgeon is able to retract the inner tube of the backflush instrument prior to pushing the backflush instrument through a valved cannula, thereby, eliminating or reducing, the likelihood of the inner tube's tip (e.g., soft tip 106) bending or shearing off when inserted through a valved cannula.

Figure 2C:
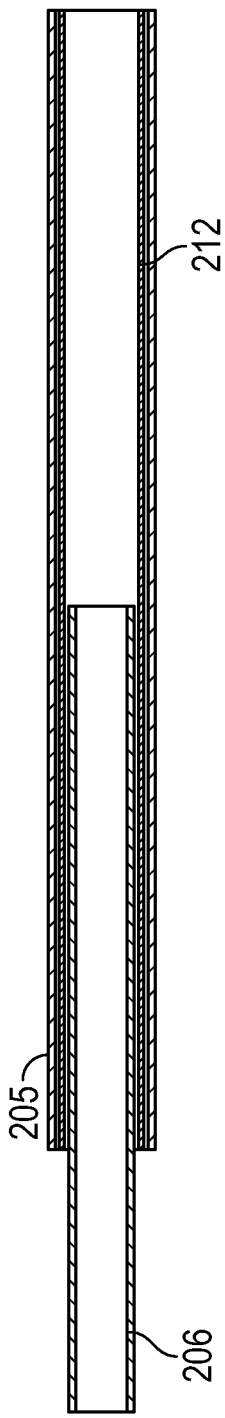
FIG. 2C is an enlarged cross-sectional view of a distal portion of FIG. 2B illustrating an extended soft tip, according to some embodiments.
Figure 2D:
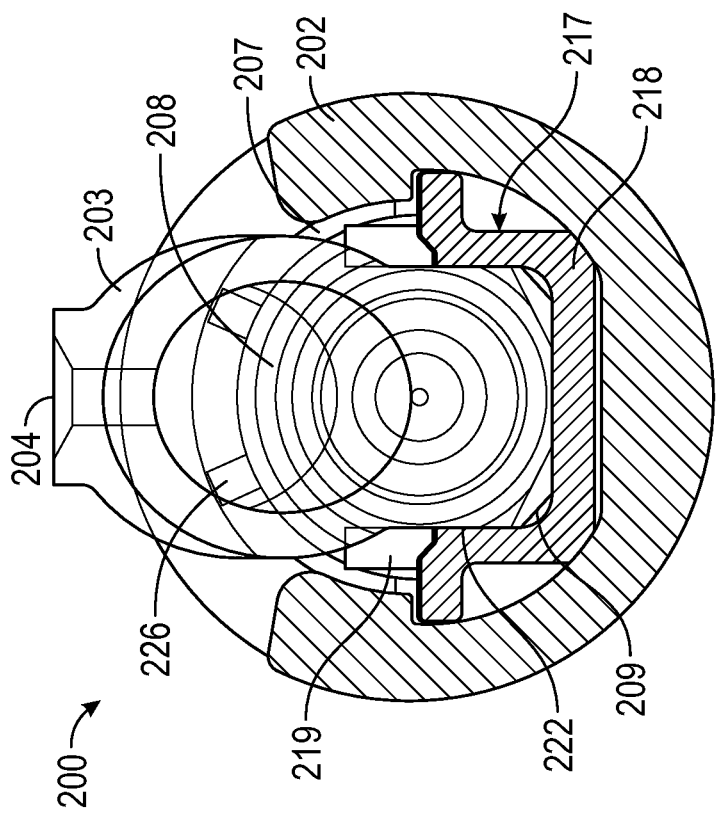
FIG. 2D is a cross-sectional view taken along section line 2D-2D of FIG. 2B showing an interior of the backflush instrument.

FIG. 2A illustrates an example retractable backflush instrument 200 in accordance with certain embodiments of the present disclosure. FIG. 2B illustrates an example cross-sectional view of backflush instrument 200. FIG. 2C is an enlarged cross-sectional view of a distal portion of FIG. 2B illustrating an extended soft tip 206. FIG. 2D is a cross-sectional view taken along section line 2D-2D of FIG. 2B showing an interior of the backflush instrument 200 along a longitudinal axis of the hand-piece 202. FIGS. 2A-2D are, therefore, described together herein for clarity.

As shown, backflush instrument 200 comprises a valve 203 housed inside the hand-piece 202 and configured to slide in relation to the hand-piece 202. The valve 203 is coupled to an adapter 208 which is coupled to a proximal end of the inner tube 212. The valve 203 is configured such that it can be pulled (e.g., by a user's finger) in a proximal direction in relation to the hand-piece 202 to retract the soft tip 206. The valve 203 is further configured such that it can be pushed (e.g., by a user's finger) in a distal direction in relation to the hand-piece 202 to extend the soft tip 206. In certain embodiments, the surgeon directly grips the valve 203 in order to pull or push the valve 203. The above described operations of pulling and pushing the valve 203 may be referred to as manual retraction and manual protraction, respectively.

As shown in FIGS. 2A and 2B, the valve 203 is in a fully extended state such that the soft tip 206 at least partially extends beyond a distal end of the outer tube 205. Retracting the valve 203 causes the inner tube to be retracted in a proximal direction, thereby, retracting soft tip 206 such that, when fully retracted, soft tip 206 would no longer extend beyond the distal end of outer tube 205. Because the surgeon puts their finger (e.g., thumb) on the valve 203 itself to retract and protract the valve 203, the surgeon is able to cover and uncover the hole 204 (e.g., with a finger) to control pressure while also retracting and extending the soft tip 206. Using this mechanism, a surgeon is able to retract soft tip 206, such as prior to pushing backflush instrument 200 through a valved cannula, thereby, eliminating or reducing the chance of damage to the soft tip 206. After pushing the backflush instrument 200 through the valved cannula, the surgeon is able to extend the soft tip 206 to enable safe contact with tissues.

As illustrated in FIG. 2B, which shows the soft tip 206 fully extended, the hand-piece 202 comprises a valve 203 that is coupled to an adapter 208 at its distal end and further coupled to a core 215 at its proximal end. The adapter 208 is slidably coupled to a proximal end of the cap 207. As used herein, the distal end of the hand-piece 202 at least includes the cap 207. The distal end of adapter 208 is coupled to a proximal end of the inner tube 212, the distal end of which is coupled to soft tip 206 that extends beyond the distal end of outer tube 205 (FIG. 2C). More specifically, at its distal end, adapter 208 comprises a cylindrical element 211 that is configured to house the proximal end of inner tube 212. In certain embodiments, a distal end of the cylindrical element 211 has a shape corresponding to an inner profile of the cap 207 for maintaining alignment between the adapter 208 and the hand-piece 202 during slidable movement of the adapter 208. In certain embodiments, inner tube 212 and cylindrical element 211 are coupled together with the use of an adhesive. In certain embodiments, inner tube 212 and cylindrical element 211 are coupled together using insert molding techniques. In certain embodiments, the proximal end of inner tube 212 is press-fitted into cylindrical element 211. In certain embodiments, the inner tube 212 may be made of polyimide or steel. Polyimide can be manufactured with smaller wall thickness providing the inner tube 212 with a larger inner diameter which enables greater flow. On the other hand, steel provides the inner tube 212 with greater total stiffness which better resists bending.

At its proximal end, adapter 208 is coupled to the distal end of valve 203, which, as described above, may be tube- or hose-shaped. As shown, the proximal end of adapter 208 comprises a cylindrical insert 210 that is configured to be inserted into the distal end of valve 203. In certain embodiments, cylindrical insert 210 and valve 203 are coupled together with the use of an adhesive. In certain embodiments, cylindrical insert 210 is press-fitted into valve 203. The adapter 208 includes a round disc 223 surrounding the adapter 208. The round disc 223 functions as an end-stop for the adapter 208. In the fully protracted position (FIG. 2B), the round disc 223 is configured to contact a plurality of notches 226 formed on the inner profile of the cap 207 to limit slidable movement of the adapter 208 in a distal direction in relation to the hand-piece 202, thereby, stopping the soft tip 206 from extending too far beyond the distal end of the outer tube 205.

As further shown in FIG. 2B, at its proximal end, the valve 203 is coupled to a distal end 214 of a core 215 which is slidably coupled to the hand-piece 202. The distal end 214 of the core 215 is configured to be inserted into the proximal end of the valve 203. At its proximal end 213, the core 215 is configured to be coupled to a connector (e.g., connector 101) for connecting the hand-piece 202 to a surgical console.

In operation, retracting valve 203 in a proximal direction causes the valve 203, core 215, adapter 208, and, therefore, soft tip 206 to slidably retract in a proximal direction in relation to the hand-piece 202. A fully retracted state is illustrated in more detail in FIGS. 3A and 3B. To extend the soft tip 206, protracting the valve 203 in a distal direction causes the valve 203, core 215, adapter 208, and, therefore, soft tip 206 to slidably extend in a distal direction in relation to the hand-piece 202.

As described above, the adapter 208 and the core 215 are configured to slidably retract and protract with the valve 203 in relation to the hand-piece 202. However, the adapter 208 and the core 215 are flexibly and indirectly coupled to each other through the valve 203, which is composed of a flexible material. In other words, rather than making a rigid connection between the adapter 208 and the core 215, the valve 203 is able to bend and/or stretch, accommodating for misalignment between the cap 207 and the hand-piece 202 and/or the core 215. The flexible material of the valve 203 allows the adapter 208 to tilt in relation to the core 215 such that the adapter 208 is able to self-align within the inner profile of the cap 207. Thus, the alignment of the adapter 208 in relation to the cap 207 is independent of the alignment between the core 215 and the cap 207. As described herein, the cap 207 is coupled to the outer tube 205, and the adapter 208 is coupled to the inner tube 212. Therefore, the alignment of the inner and outer tubes 212, 205 depends directly on the alignment between the adapter 208 and the cap 207. Therefore, the flexible and indirect coupling of the adapter 208 and the core 215 described herein, reduces friction and sticking of the inner tube 212 sliding within the outer tube 205 by improving the alignment therebetween.

As will be described in more detail below, in the fully protracted position, the core 215 has an end-stop contacting the hand-piece 202 which is separate from the end-stop provided between the adapter 208 and cap 207. The end-stop mechanism associated with the core 215 refers to a distal end of projection 220 formed on slider 217 contacting a distal shoulder 224 of channel 221 formed in hand-piece 202, as further described below with respect to FIG. 2B. The end-stop provided between the adapter 208 and the cap 207 refers to the round disc 223 of the adapter 208 contacting the plurality of notches 226 formed on the inner profile of the cap 207, as described above with respect to FIG. 2B. The end-stops of the adapter 208 and the core 215 which limit movement of the respective components in the distal direction in relation to the hand-piece 202 are decoupled from each other. The decoupling of the end-stops enables the end-stop provided by the core 215 to provide the user with a defined end-stop feeling when moving to the fully protracted position while also allowing misalignment of the cap 207 in relation to the hand-piece 202 and/or the core 215 as described above.

As further shown in FIG. 2B, at its distal end, the core 215 is coupled to a slider 217 which is configured to slidably support the valve 203. Details of the slider 217 are more clearly depicted in FIG. 2D which illustrates a cross-sectional view taken along section line 2D-2D of FIG. 2B. The slider 217 comprises a body portion 218 and a pair of sidewalls 219 extending longitudinally from a proximal end of the body portion 218 to the distal end 214 of the core 215. A slot 222 is formed between the pair of sidewalls 219 for receiving a generally square-shaped base 209 of the valve 203. The slot 222 houses the square-shaped base 209 of the valve 203 to prevent relative movement between the valve 203 and the slider 217. For example, the valve 203 may be prevented from rotating or being pushed down too far into the hand-piece 202.

As further shown in FIG. 2B, in certain embodiments, a projection 220 extends radially from the body portion 218 and is received within a channel 221 formed in the hand-piece 202. The projection 220 and corresponding channel 221 are configured to help maintain rotational alignment and prevent jamming of the slider 217, valve 203, and core 215 against the hand-piece 202 during slidable movement. The projection 220 and corresponding channel 221 are configured to limit the extent of slidable movement of the slider 217, valve 203, and core 215 in relation to the hand-piece 202. More specifically, when the valve 203 is fully protracted, a distal end of the projection 220 contacts a distal shoulder 224 of the channel 221, thereby, preventing further slidable movement of the slider 217, valve 203, and core 215 in the distal direction in relation to the hand-piece 202 (FIG. 2B). Furthermore, when the valve 203 is fully retracted, a proximal end of the projection 220 contacts a proximal shoulder 225 of the channel 221 preventing further slidable movement of the slider 217, valve 203, adapter 208, and core 215 in the proximal direction in relation to the hand-piece 202 (FIG. 3A).

Although FIG. 2B shows adapter 208 and valve 203 as separate components, in certain embodiments, adapter 208 and valve 203 may be manufactured as one piece. For example, both adapter 208 and valve 203 may be made from the same material. In another example, adapter 208 and valve 203 may be manufactured in a two-component injection molding process. Also, although FIG. 2B shows core 215 and slider 217 manufactured as one piece, in certain embodiments, core 215 and slider 217 may be manufactured as separate pieces. Note that whether core 215 and slider 217 are manufactured as different pieces or the same piece, they are referred to herein as being coupled to each other. Also, although FIG. 2C shows soft tip 206 and inner tube 212 as separate components that are attached together, in certain embodiments, inner tube 212 and soft tip 206 may be manufactured as one piece using the same material. In such embodiments, inner tube 212 is also made of flexible and soft material (e.g., silicone, PUR, etc.). Note that whether inner tube 212 and soft tip 206 are manufactured as different pieces or the same piece, they are referred to herein as being coupled to each other.

FIG. 3A illustrates an example cross-sectional view of backflush instrument 200 in a fully retracted state. As shown in FIG. 3A, retraction of the valve 203 in the proximal direction has caused the valve 203, adapter 208, core 215, and slider 217 to slidably retract in a proximal direction in relation to the hand-piece 202. In the fully retracted state, the proximal end 213 of the core 215 has extended further outside the hand-piece 202 in the proximal direction compared to the fully extended state (FIG. 2B). As shown in FIG. 3A, the proximal end of the projection 220 is in contact with the proximal shoulder 225 of the channel 221 preventing further slidable movement of the valve 203, adapter 208, core 215, and slider 217 in the proximal direction in relation to the hand-piece 202. The length of the channel 221 is configured such that the adapter 208 does not fully disengage the inner profile of the cap 207. In other words, the projection 220 contacts the proximal shoulder 225 before the adapter 208 disengages the cap 207 which could result in jamming of the adapter 208. As shown in FIG. 3B, the soft tip 206 is completely retracted into the outer tube 205.

Although the illustrated embodiments demonstrate extension of the soft tip 206 caused by manual protraction of the valve 203, adapter 208, and core 215, in some other embodiments, protraction of the valve 203 is actuated by energy stored during the retraction step. For example, in certain embodiments, retracting the valve 203 in the proximal direction compresses valve 203, which is made of flexible and/or compressible material. For example, valve 203 may be made of silicone. In certain embodiments, compression of the valve 203 may occur along a portion of the valve 203 located between the hole 204 and the proximal end of the valve 203. Thus, when a retracted valve 203 is released, valve 203 automatically decompresses (e.g., based on spring force) and pushes the valve 203, adapter 208, and core 215 back to their original positions, thereby, causing soft tip 206 of inner tube 212 to extend beyond the distal end of the outer tube 205, as shown in FIG. 2C. In some other embodiments, the backflush instrument may be configured with a spring (e.g., a coil spring) for protracting the valve 203, adapter 208, and core 215. For example, a spring may be located between a portion of the hand-piece 202 and one of the core 215, slider 217, or projection 220 for biasing the core 215 in a distal direction in relation to the hand-piece 202.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An apparatus for use in an ophthalmic surgical procedure, comprising:
   a hand-piece;
   an outer tube having a proximal end coupled to a distal end of the hand-piece;
   an inner tube housed within the outer tube and having a distal end coupled to a soft tip and a proximal end coupled to an adapter, wherein in a fully extended state, the soft tip at least partially extends beyond a distal end of the outer tube;
   the adapter slidably coupled to the distal end of the hand-piece, the adapter having a proximal end coupled to a distal end of a valve and a distal end coupled to the proximal end of the inner tube;
   the valve housed inside the hand-piece and having the distal end coupled to the proximal end of the adapter; and
   a core housed by and slidably coupled to the hand-piece, the core having a distal end coupled to a proximal end of the valve;

wherein to retract the soft tip, the valve is retracted, causing the adapter, the valve, and the core to slidably retract in a proximal direction in relation to the hand-piece, and
   wherein to extend the soft tip, the valve is protracted, causing the adapter, the valve, and the core to slidably protract in a distal direction in relation to the hand-piece.

2. The apparatus of claim 1, wherein the distal end of the core is configured to be inserted into the proximal end of the valve, and wherein a proximal end of the core is configured to be coupled to a connector for connecting the hand-piece to a surgical console.

3. The apparatus of claim 2, further comprising:
   a slider configured to slidably support the valve, the slider comprising:
      a body portion disposed below the valve; and
      a pair of sidewalls extending longitudinally from a proximal end of the body portion to the distal end of the core.

4. The apparatus of claim 3, wherein a slot is formed between the pair of sidewalls, the slot configured to house a base of the valve to prevent relative movement between the valve and the slider.

5. The apparatus of claim 3, wherein the slider further comprises a projection extending from the body portion, wherein the projection is received within a channel formed in the hand-piece for limiting longitudinal extension and retraction of the soft tip.

6. The apparatus of claim 5, wherein the channel formed in the hand-piece has shoulders formed at opposite longitudinal ends thereof, and wherein contact between the projection and each of the shoulders is configured to limit extension and retraction of the soft tip.

7. The apparatus of claim 5, wherein in the fully extended state, a distal end of the projection contacts a distal shoulder of the channel preventing further slidable movement of the valve and the core in the distal direction in relation to the hand-piece, and wherein in a fully retracted state, a proximal end of the projection contacts a proximal shoulder of the channel preventing further slidable movement of the adapter, the valve, and the core in the proximal direction in relation to the hand-piece.

8. The apparatus of claim 1, wherein the apparatus comprises a backflush instrument.

9. The apparatus of claim 1, wherein the adapter comprises:
   a cylindrical insert configured to be inserted into the distal end of the valve; and
   a cylindrical element configured to house the proximal end of the inner tube.

10. The apparatus of claim 9, wherein a distal end of the cylindrical element has a shape corresponding to an inner profile of a cap for maintaining alignment between the adapter and the hand-piece during slidable movement of the adapter.

11. The apparatus of claim 1, wherein retracting and protracting the valve causes the pressure to be controlled.

12. The apparatus of claim 1, further comprising a cap having a plurality of notches formed on an inner profile thereof, wherein a round disc surrounding the adapter is configured to contact the plurality of notches to limit slidable movement of the adapter in the distal direction in relation to the hand-piece.

13. The apparatus of claim 12, wherein the adapter and the core are flexibly and indirectly coupled to each other, and wherein the flexible and indirect coupling is configured to allow the adapter to tilt in relation to the core for self-aligning the adapter within the inner profile of the cap.

* * * * *